(12) United States Patent
Spangler

(10) Patent No.: US 10,772,570 B2
(45) Date of Patent: Sep. 15, 2020

(54) NON?INVASIVE PREDICTION OF RISK FOR SUDDEN CARDIAC DEATH

(71) Applicant: SPANGLER SCIENTIFIC LLC, New York, NY (US)

(72) Inventor: Gregory J. Spangler, New York, NY (US)

(*) Notice: Subject to any disclaimer, the term of this patent is extended or adjusted under 35 U.S.C. 154(b) by 168 days.

(21) Appl. No.: 15/759,386

(22) PCT Filed: Sep. 13, 2016

(86) PCT No.: PCT/US2016/051460
§ 371 (c)(1),
(2) Date: Mar. 12, 2018

(87) PCT Pub. No.: WO2017/048684
PCT Pub. Date: Mar. 23, 2017

(65) Prior Publication Data
US 2018/0249965 A1    Sep. 6, 2018

Related U.S. Application Data

(60) Provisional application No. 62/220,462, filed on Sep. 18, 2015.

(51) Int. Cl.
*A61B 5/00* (2006.01)
*A61B 5/0402* (2006.01)
(Continued)

(52) U.S. Cl.
CPC .......... *A61B 5/7275* (2013.01); *A61B 5/0402* (2013.01); *A61B 5/04017* (2013.01);
(Continued)

(58) Field of Classification Search
CPC ........ G16H 50/50; G16H 50/30; G16H 40/60; A61B 5/04017; A61B 5/0402;
(Continued)

(56) References Cited

U.S. PATENT DOCUMENTS

| 2003/0100924 A1 | 5/2003 | Foreman et al. |
| 2005/0004485 A1 | 1/2005 | Crosby et al. |

(Continued)

OTHER PUBLICATIONS

PCT Notification of Transmittal of International Preliminary Report on Patentability issued in corresponding PCT application No. PCT/US16/51460 dated Jun. 28, 2018.
(Continued)

*Primary Examiner* — Erin M Piateski
(74) *Attorney, Agent, or Firm* — Botos Churchill IP Law LLP

(57) ABSTRACT

A method and apparatus for the quantitative determination of an individual's risk for sudden cardiac death (SCD) is described. Risk determination is accomplished and may have a sensitivity and specificity of greater than 95%, by generating linear and nonlinear mathematical digital ECG-constructed models from digital ECG-type data of an individual's digital ECG, determining stability/instability of digital ECG-constructed control model systems corresponding to the digital ECG-constructed models by a plurality of techniques and transforming stability/instability values obtained by the determining stability/instability into a quantitative value reflecting an individual's risk for SCD.

20 Claims, 7 Drawing Sheets

(51) Int. Cl.
*A61B 5/04* (2006.01)
*A61B 5/0452* (2006.01)
*G01N 33/68* (2006.01)
*G01N 33/53* (2006.01)
*A61B 5/0464* (2006.01)
*G01N 33/574* (2006.01)
*G16H 40/60* (2018.01)
*G16H 50/30* (2018.01)
*G16H 50/50* (2018.01)

(52) U.S. Cl.
CPC .......... *A61B 5/0452* (2013.01); *A61B 5/0464* (2013.01); *A61B 5/7207* (2013.01); *G01N 33/53* (2013.01); *G01N 33/57407* (2013.01); *G01N 33/57434* (2013.01); *G01N 33/68* (2013.01); *G16H 40/60* (2018.01); *G16H 50/30* (2018.01); *G16H 50/50* (2018.01); *A61B 5/725* (2013.01)

(58) Field of Classification Search
CPC ... A61B 5/0452; A61B 5/0464; A61B 5/7207; A61B 5/725; G01N 33/53; G01N 33/57407; G01N 33/57434; G01N 33/68

USPC ........................................................ 600/509
See application file for complete search history.

(56) References Cited

U.S. PATENT DOCUMENTS

| 2010/0217144 | A1* | 8/2010 | Brian ................... A61B 5/0452 600/523 |
| 2012/0179055 | A1* | 7/2012 | Tamil ................... A61B 5/0452 600/509 |
| 2013/0268013 | A1 | 10/2013 | Sanghera et al. |
| 2015/0216426 | A1 | 8/2015 | Burton |

OTHER PUBLICATIONS

"PCT Search Report dated Nov. 18, 2016".
Chen, Xiaozhon et al. A Novel Methodology for Assessing the Bounded-Input Bounded-Output Instability in QT Interval Dynamics: Application etc. IEEE Transactions on Biomedical Engineering, IEEE Service Center, vol. 59, No. 8, Aug. 1, 2012.
EP Search Report dated Mar. 28, 2019, EP Application No. 16847122.5.

* cited by examiner

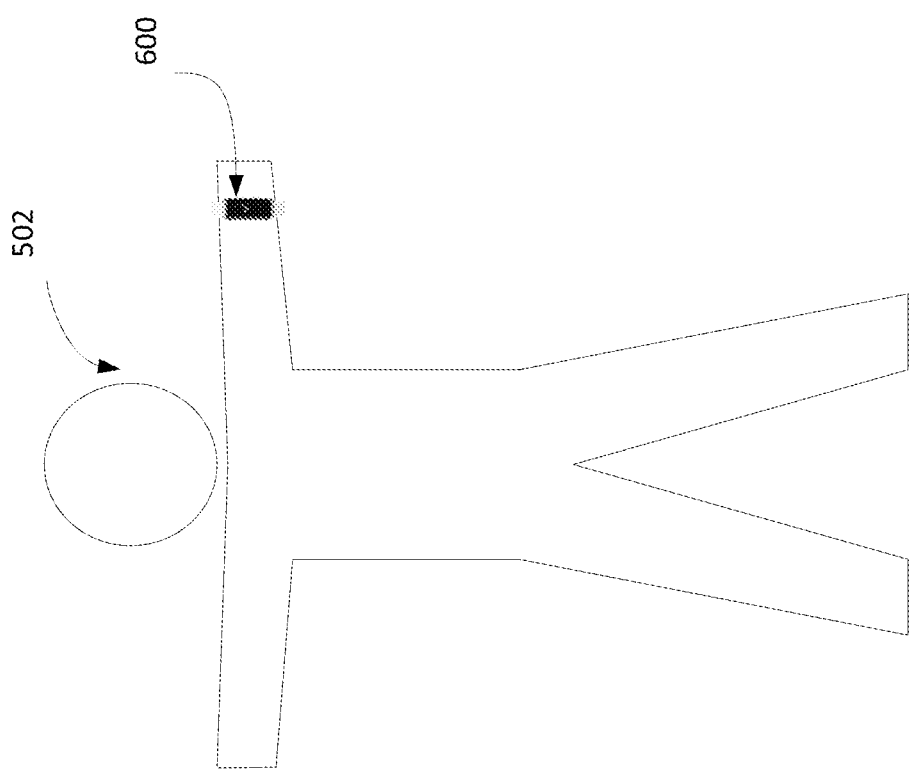

NON-INVASIVE PREDICTION OF RISK FOR SUDDEN CARDIAC DEATH

CROSS-REFERENCE TO RELATED APPLICATIONS

The present application is a national phase entry under 35 U.S.C. § 371 of International Application No. PCT/US2016/051460 filed Sep. 13, 2016, published in English, which claims priority from U.S. Provisional Patent Application No. 62/220,462 filed Sep. 18, 2015, all of which are incorporated herein by reference.

FIELD OF THE TECHNOLOGY

The present technology relates to a method for quantitative determination of any individual's risk for sudden cardiac death (SCD), which is also often referred to as sudden cardiac arrest (SCA) or massive heart attack. More specifically, the present technology may relate to a noninvasive apparatus, system, device and method, such as using digitized electrocardiogram (ECG) data from a standard resting ECG, to accurately, rapidly, in near-real time, and easily identify in a quantitative manner individuals at risk for sudden cardiac death with high sensitivity and high specificity.

BACKGROUND OF THE TECHNOLOGY

Sudden cardiac death (SCD) is defined as the unexpected death due to cardiac causes of persons with or without underlying cardiac disease, with no other known cause for death. SCD occurs within a short period of time, for example, generally within one hour, following the onset of symptoms (if any symptoms are encountered).

SCD is a major public health problem as it has reached epidemic proportions, responsible for at least 325,000 deaths per year in the United States alone. (See Goldberger. Circulation. 2008; 118:000-000; Zipes, D. P., et al., *ACC/AHA/ESC 2006 Guidelines for Management of Patients With Ventricular Arrhythmias and the Prevention of Sudden Cardiac Death—Executive Summary*. Circulation, 2006: p. CIRCULATION AHA.106.178104.). SCD is the second leading cause of death in the U.S., responsible for slightly less deaths than myocardial infarction. Despite the decreased incidence of all cardiac deaths secondary to improved medical treatment, SCD continues to represent about half of all cardiac deaths. (See Ezekowitz. *Ann Intern Med*. August 2007; 21; 147(4):251-62).

Most cases of SCD are related to cardiac ventricular arrhythmias (ventricular tachycardia, or VT). Coronary artery disease is associated with the largest number of SCDs. Acute coronary syndrome (ACS) can lead to malignant arrhythmias that are the result of ischemia. Additionally, coronary artery disease (CAD) may lead to microscopic or macroscopic scar formation that can represent substrate for malignant arrhythmias.

Congestive Heart Failure (CHF) with or without CAD is another cardiac illness associated with a significant risk for SCD. In addition, cardiomyopathy, left ventricular hypertrophy (LVH), myocarditis, hypertrophic cardiomyopathy, congenital coronary artery anomalies, and myxomatous mitral valve disease are associated with an increased SCD risk. Finally, the presence of channelopathies such as Brugada syndrome and congenital heart disease or acquired long QT syndrome, idiopathic ventricular fibrillation (VF), Arrhythmogenic Right Ventricular Cardiomyopathy (ARVC), catecholaminergic VT, and Wolff-Parkinson-White (WPW) syndrome increase the risk of SCD.

Implantable cardioverter-defibrillator (ICD) therapy has significantly decreased the occurrence of SCD in high-risk patients, but has done little to reduce the overall incidence of SCD nationally. (See Bardy. N Engl J Med. 2005 Jan. 20; 352(3):225-37). This is explained by the fact that two-thirds of patients suffering SCD are in low or intermediate risk groups, resulting in the greatest absolute number of patient deaths. However, multiple trials have repeatedly demonstrated that patients in low and intermediate risk groups do not benefit from prophylactic ICD placement. This result demonstrates the lack of sensitivity and specificity of contemporary methods used to stratify individuals for SCD risk. The ability to prevent SCD using ICDs is of great importance, and it demonstrates the critical need for a highly sensitive and highly specific method for identifying individuals at risk for SCD.

Based on the foregoing, the identification of individuals presently considered to have no, low, or intermediate risk for SCD as defined by presently available risk-stratification methods—but in reality are at high risk—continues to be a major public health concern.

Presently available techniques for the identification of individuals at risk for SCD include medical history, (e.g., history of coronary artery disease (CAD), congestive heart failure (CHF), decreased left ventricular ejection fraction (LVEF), prior myocardial infarction, structural or ischemic heart disease), Holter monitoring, heart rate variability analysis, signal averaged electrocardiography (SAECG), microvolt T-wave alternans analysis, ambulatory ECG monitoring, metabolic factors and/or parasympathetic tone, heart rate turbulence studies, baroreceptor sensitivity studies and the presence of myocardial scar as detected using magnetic resonance imaging (MRI). Severely reduced LVEF and the presence of advanced CHF (NYHA Class III or IV) currently serve as the main identifiers for patients at high-risk for SCD and, therefore, for identifying who may benefit from ICD therapy. (See Epstein. Heart Rhythm. 2008 June; 5(6):934-55; Chugh. Nat Rev Cardiol. 2010 Jun. 7 (6): 318-326, available at http://www.ncbi.nlm.nih. gov/pmc/articles/PMC3052394/). However, no presently available method, including those listed above, alone or in combination, has clinically acceptable sensitivity or specificity for the identification of individuals at risk for SCD. A detailed discussion of some exemplary techniques is provided herewith.

Left Ventricular Ejection Fraction and NYHA Class III or IV CHF

Left ventricular ejection fraction (LVEF), as evaluated by one of many modalities, and the presence of NHHA Class III or Class IV CHF are the two major predictors of SCD. They are presently the two principle indications used to determine which patients are candidates for ICD placement. (Of course, a history of a prior SCD event is an absolute indication for ICD placement.) (See Epstein. Heart Rhythm. 2008 June; 5(6):934-55; Rouleau. J Am Coll Cardiol 1996; 27:1119-27). Assessment of ejection fraction (EF) has multiple advantages such as accessibility, ease of use, and relative reproducibility and has been the major determinant of patients who are considered for prophylactic ICD implantation. Several trials that have found that an LVEF≤35%, particularly with symptoms of heart failure (CHF, Class III or IV), have served as the accepted marker for identifying high-risk patients. (Bardy. N Engl J Med. 2005 Jan. 20;

352(3):225-37). Conversely, multiple studies have found an LVEF≥40% is not an accurate marker for those at increased risk for SCD. This finding suggests that EF may be less useful as a marker for SCD once the EF is greater than 40% on a population basis. (See Ikeda. J AmColl Cardiol 2006; 48:2268-74).

Randomized clinical trials concerning prophylactic ICD implantation have evaluated patients with depressed LVEF. The implications of these studies in the treatment of SCD are limited since most cases of SCD do not occur in patients with low LVEF. (See Zipes, D. P., et al., *ACC/AHA/ESC 2006 Guidelines for Management of Patients With Ventricular Arrhythmias and the Prevention of Sudden Cardiac Death—Executive Summary*. Circulation, 2006: p. CIRCULATION AHA.106.178104). Studies such as multicenter automatic defibrillator implantation trial I (MADIT I), MADIT II and sudden cardiac death in heart failure trial (SCD-HeFT) have all shown significant reductions in arrhythmic and overall mortality with ICD therapy in patients with severely decreased LVEFs. However, the majority of patients who were evaluated, and showed benefit from the prophylactic ICD implantation, had LVEFs≤25%, limiting the ability to extrapolate this data to the low and intermediate risk groups.

Analysis of the multicenter unsustained tachycardia trial (MUSTT) demonstrates that LVEF does not, in fact, represent the greatest risk of total and arrhythmic death. New York Heart Association (NYHA) class, history of heart failure, non-sustained VT, enrollment as inpatient, and atrial fibrillation all portended greater risk as individual markers. Patients with LVEF<30% but with no other risk factors may have a lower predicted mortality risk than patients with LVEF>30% as well as other risk factors. Risk of SCD in patients with cardiomyopathy depends on multiple variables in addition to LVEF and may be further elucidated using other methods. (See Salerno-Uriarte. J Am Coll Cardiol 2007; 50:1896-904). Overall, EF<35% and/or the presence of Class III or Class IV CHF are important criteria (although present in only a minority of SCD patients) for ICD placement. However, although they are the best presently available methods for SCD risk prediction, they—alone or in combination with other methods—suffer from unacceptably low sensitivity and specificity.

Signal-Averaged Electrocardiogram

In patients with VT, areas of scar may result in slow conduction and prolonged activation of segmental regions of the ventricle. This slowing may manifest itself as ventricular late potentials which are low-amplitude signals that occur after the end of the QRS complex and are thought to reflect slow and fragmented myocardial conduction. (See Simson. Am J Cardiol 1983; 51:105-112). Late potentials have been correlated with abnormal signals found during electrophysiological studies in segmental sections of the endocardium and represent slowly activated tissue that can represent substrate for reentry. (See Simson. Am J Cardiol 1983; 51:105-112).

Signal averaged electrocardiography (SAECG) is a technique where multiple QRS complexes are digitized, averaged, filtered, and further processed with spectral analysis to facilitate late potential analysis. The sensitivity and specificity of an abnormal SAECG for the prediction of SCD or arrhythmic events has been reported to vary from 30% to 76% and the specificity from 63% to 96% (Bailey. J Am Coll Cardiol 2001; 38:1902-1911). Conversely, the negative predictive value is high, exceeding 95%, also reflecting the low prevalence of SCD.

There are limited data evaluating the prognostic value of SAECG in patients with an LVEF greater than 35% and what data exists has been inconsistent (Ikeda. J AmColl Cardiol).

Microvolt T-Wave Alternans

Microvolt T-wave alternans (MTWA) is a technique developed to identify instability of ventricular repolarization during exercise. This instability can lead to dispersion of ventricular refraction, and has been promoted as another methodology for risk stratification for SCD. (See Pastore. Circulation 1999; 99:1385-94; Verrier, R. L., et al., *Microvolt T-wave alternans physiological basis, methods of measurement, and clinical utility—consensus guideline by International Society for Holter and Noninvasive Electrocardiology*. J Am Coll Cardiol, 2011. 58(13): p. 1309-24).

A large meta-analysis has shown prognostic value of a negative MTWA test in post-myocardial infarction (post-MI) patients with reduced ejection fraction, with the strength of the test resulting mainly from a very high negative predictive value (See Gehi. J Am Coll Cardiol 2005; 46:75-82). Additional studies evaluating the prognostic value of MTWA have been inconsistent (See Salerno-Uriarte. J Am Coll Cardiol 2007; 50:1896-904; J Am Coll Cardiol 2007; 50:1896-904).

In a large Italian study, more than 400 patients were tested for MTWA and followed over 18-24 months revealing a negative predictive value of 97%. However, the patients who tested positive for MTWA represented a group who had concomitantly been diagnosed with either non-ischemic cardiomyopathy, NYHA Class II/III CHF, or a LVEF less than 40%, representing a group of patients already at high risk for SCD and adding little benefit to a low or intermediate risk population. The evidence for usefulness of MTWA in this population is not well-established and has generally been limited by poor positive predictive values due to low prevalence (See Ikeda. J AmColl Cardiol 2006; 48:2268-74).

Ambulatory ECG Monitoring

The detection of ventricular arrhythmias (including premature ventricular contractions (PVCs) and non-sustained ventricular tachycardia (NSVT)) using ambulatory ECG monitoring in patients with left ventricular dysfunction following myocardial infarction is associated with an increased risk for mortality (See Bigger. Circulation 1984; 69:250-8).

However, there is no significant increased value of ambulatory ECG monitoring for risk-stratification in high-risk patients. (See Bardy. N Engl J Med. 2005 Jan. 20; 352(3): 225-37; Moss. N Engl J Med, Vol. 346, No. 12).

Given currently available data, when evaluating the risk of SCD in patients without severe LV systolic dysfunction, the value of ambulatory ECG testing is inconclusive and the low positive predictive value of identifying NSVT in this patient population may limit its clinical utility. (See Maggioni. Circulation 1993; 87:312-22).

Heart Failure

The clinical syndrome of congestive heart failure (CHF) can contribute to arrhythmogenesis in patients with ventricular dysfunction and can increase mortality in patients regardless of LVEF.

Patients with NYHA Class I and II symptoms have been shown to have low overall death rates. However, 67% of total deaths were due to SCD. In contrast, among studies with a mean functional Class IV, there was a high total mortality, but the fraction of SCD was only 29% as the incidence of progressive pump failure increased. (See Goldberger. Circulation. 2008; 118:000-000). This paradox continues to have major implications on the current utility of ICDs in the low and intermediate population.

Heart failure classification is often dynamic in nature depending on the modality at the time, volume status, medications used at the time, and other comorbid conditions that could influence functional status, thereby limiting its utility.

Metabolic Factors

Factors related to ventricular arrhythmias and SCD include serum catecholamine levels and electrolyte imbalances. Manifestations of neurohormonal activation, such as hyponatremia and increased plasma norepinephrine, renin, and natriuretic peptide levels, have been found to be predictive of mortality as well. (See Pratt. Circulation 1996; 93:519-524).

Autonomic Control

Autonomic imbalance has been implicated in SCD, possibly due to reduced vagal tone and sympathetic enhancement, favoring the formation of life-threatening arrhythmias. Markers of autonomic control, such as heart rate variability (HRV), baroreflex sensitivity (BRS), and heart rate turbulence (HRT), have been found to have independent and in some cases additive prognostic value for SCD. While this effect is more prominent in patients with a reduced ejection fraction, some trials showed significant risk even for patients with relatively preserved EF. (See Lombardi. Cardiovasc Res (2001) 50 (2): 210-217).

Numerous studies have explored the prognostic value of HRV parameters for predicting outcomes in postinfarction patients and have consistently shown depressed HRV is associated with increased mortality. (See Lombardi. Cardiovasc Res (2001) 50 (2): 210-217). However, data regarding the prognostic significance of HRV for predicting SCD in patients with ischemic heart disease is lacking, and serves no role in risk-stratification. All data to date concerning autonomic control in patients with a relatively preserved LVEF has not proven significant. (See De Ferrari. J Am Coll Cardiol 2007; 50:2285-90).

Based on the foregoing, at present there are no methods with acceptable sensitivity or specificity to be clinically useful in the identification of people at risk for SCD. There is a critical need for a device able to identify individuals at risk for SCD (independent of any underlying pathology) with high sensitivity and specificity. This is particularly true because there are presently available technologies able to prevent SCD in individuals at risk (e.g., ICDs). There is also a great need to accurately identify patients in currently recognized high-risk groups for SCD who would not benefit (and possibly suffer) from high-cost ICD placement.

Point of convention: In the literature, the term Sudden Cardiac Death (SCD) refers to 1) the occurrence of those ventricular arrhythmias which, if not immediately and successfully treated (e.g., by an external or implantable cardioverter-defibrillator) lead to death or 2) the death of an individual from such a ventricular arrhythmia. In contrast, some authors refer to the occurrence of these most often lethal ventricular arrhythmias as Sudden Cardiac Arrest (SCA), and use the term SCD specifically in those cases in which the arrhythmic event results in death. Throughout the remainder of this specification, the first and more commonly used convention is intended.

BRIEF SUMMARY OF THE TECHNOLOGY

The present technology relates to a non-invasive, quantitative risk stratification methodology for determining an individual's risk for SCD. The input data for the methodology described is digitized ECG data.

In accordance with one aspect of the technology, a method for quantitative stratification of sudden cardiac death (SCD) risk using digital electrocardiogram (ECG)-type data is obtained from an individual. The technology may begin with the preprocessing of such digital ECG input data. Such preprocessing may include denoising, detrending and normalization. A plurality of mathematical models may then be constructed corresponding to the data from each input ECG lead. Control model systems may then be constructed to correspond to each model. Using a plurality of techniques, the relative stability/instability of each control model system may be determined. The calculated system stabilities (for all systems corresponding to all ECG leads of any given individual) may be combined into an overall stability/instability measure. Finally, the overall stability/instability measure may be converted into a value which corresponds to the individual's risk for SCD.

In one embodiment, digital ECG data from an individual may be obtained from a single lead, three lead, or twelve lead ECG sensor or ECG machine.

In some cases, the method may further include preprocessing, with a preprocessor, such as a processor that detrends (removing baseline wander), denoises (removing noise from electrical, mechanical, respiratory, white noise sources, etc.) and normalizes. Methods used for denoising may include wavelet packet techniques.

In accordance with an aspect of the technology, an apparatus for quantitative stratification of sudden cardiac death (SCD) risk using digital electrocardiogram (ECG)-type data of an individual, may include circuitry configured to control: preprocessing input digital ECG-type data taken from the individual to detrend, denoise, and normalize in order to obtain preprocessed ECG-type data; generating a plurality of mathematical ECG-derived models corresponding to the preprocessed ECG-type data; generating ECG-derived control model systems corresponding to each ECG-derived model; determining system stabilities of the ECG-derived control model systems, by a plurality of techniques which may include analyzing responses of the ECG-derived control model systems to a plurality of impulses; and determining, based on the systems stabilities, a derived SCD risk for each individual's ECG.

In accordance with an aspect of the technology, a non-transitory storage medium may include a program executable by a computer. The program may include preprocessing digital ECG-type data by detrending, denoising, and normalizing, to obtain preprocessed ECG-type data; generating a plurality of mathematical ECG-derived models corresponding to the preprocessed ECG-type data; generating ECG-derived control model systems corresponding to each ECG-derived model; determining system stabilities of the ECG-derived control model systems by a plurality of techniques; and determining, based on the system stabilities, a derived SCD risk for the individual.

A beneficial application of the present technology is a method, such as in a processor or other processing apparatus, for determining an individual's risk for SCD, such as with high sensitivity and specificity (e.g., greater than about 95%) with p-value <0.001.

BRIEF DESCRIPTION OF THE DRAWINGS

The present technology is illustrated by way of example, and not by way of limitation, in the figures of the accompanying drawings, in which like reference numerals refer to similar elements including:

FIG. 7 is an exemplary implementation of a SCD risk determination apparatus in accordance with the present technology.

DETAILED DESCRIPTION

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description provides specific details of aspects of the technologies detailed herein. The headings and subheadings provided herein are for convenience and ease of reading only.

1. Overview

The present technology described herein generally relates to quantitatively identifying any individual's risk for Sudden Cardiac Death (SCD), which may also be termed Sudden Cardiac Arrest (SCA), using noninvasive methods. Such noninvasive mechanisms may include the design of linear and nonlinear mathematical models using input digital electrocardiogram (ECG)-type data obtained from any given individual. In one embodiment, at least one digital ECG lead may be used for data input and modeling ECG-derived models and constructing ECG-derived control model systems. The present technology may include determining stability of ECG-derived control model systems, which have been generated by incorporating system control operation into the ECG-derived models respectively, in part by analyzing responses of the ECG-derived models to perturbations simulating electrical impulses; and determining, based on the stability determinations, whether the ECG-derived control model systems indicate high risk of occurrence of lethal ventricular arrhythmias or SCD for the patient.

Specifically, to design an ECG-derived model, the noninvasive mechanisms discussed herein may analyze digital input ECG-type data from any individual, such as a patient in a study including several test groups of patients.

The input digital ECG-type data may, for example, be obtained from a standard, resting 12-lead ECG machine, or, alternatively, from a single, three, or twelve skin-potential sensors in the complete absence of any ECG machine. This data in all cases is obtained in a noninvasive manner.

The ECG-derived mathematical models constructed for quantitative risk determination may be designed by the model processor through the use of linear and nonlinear mathematical modeling techniques, to obtain linear and nonlinear ECG-derived models.

In one embodiment, the ECG-derived models may be constructed for each patient in a study. The ECG-derived models are unique for each patient/ECG, and may be generated to represent conduction of electrical impulses in the myocardium.

Figure 1:
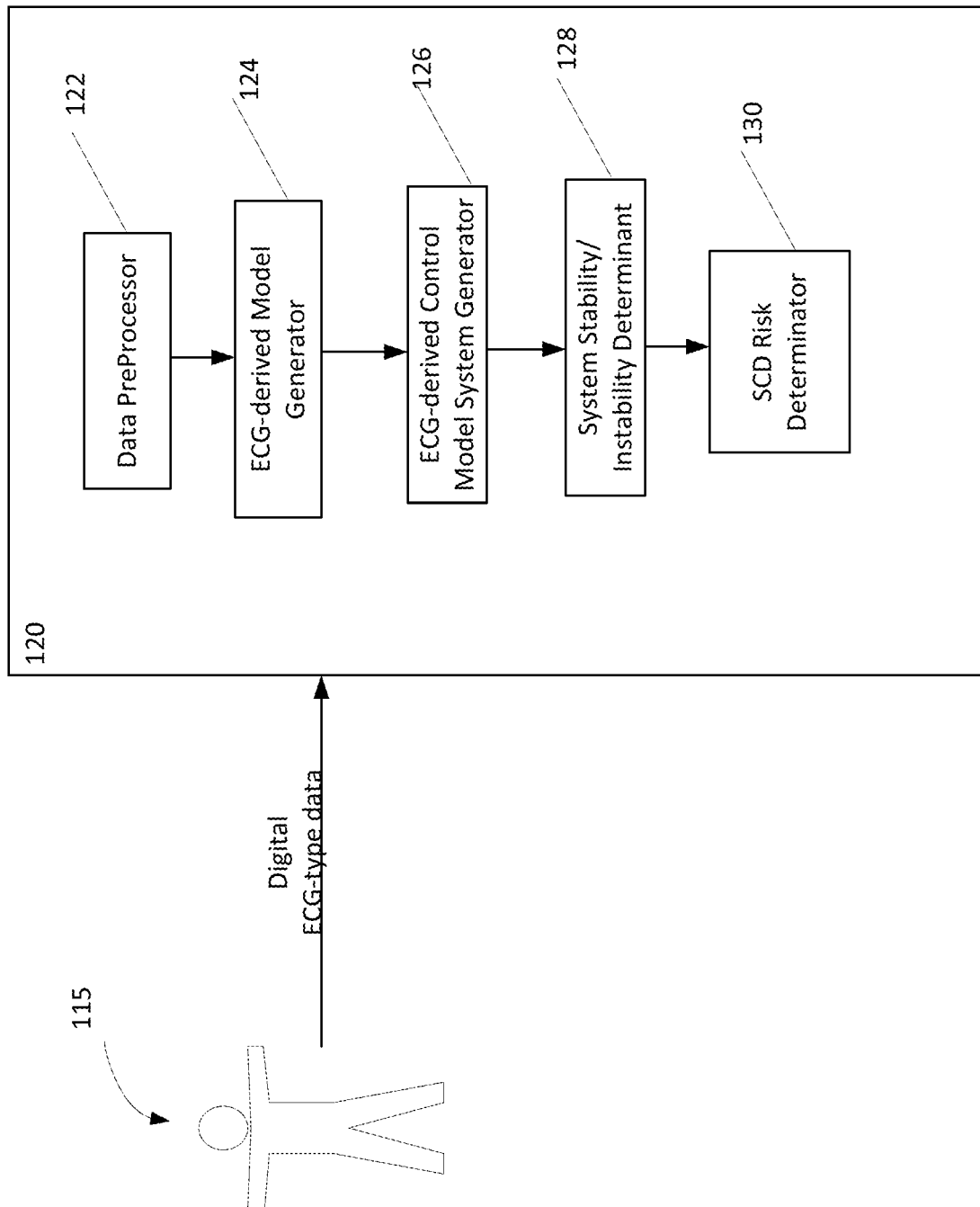
FIG. 1 is an illustrative overview of an SCD risk determination apparatus for determining SCD risk from input digital ECG-type data obtained from an individual in accordance with the present technology.

A single or numerous ECG-derived model(s) are derived using a variety of System Identification (SI) based techniques. A Control Model System is constructed to correspond to each model. The electrical stability of each ECG-derived control model system may then be determined by analysis of the impulse response of each ECG-derived control model system. Time as well as frequency properties of the impulse, may be used in this calculation. In addition, system stability margin methods may be used in stability determination. For each individual, stability values may be used to determine the overall risk By way of illustration, FIG. 1 shows an example operating environment of the present technology. The present technology may include a SCD risk determination apparatus 120 including a data preprocessor 122, an ECG-derived model generator 124, an ECG-derived control model system generator 126, a system stability/instability determinant 128 and an SCD risk determiner 130. The apparatus may require as input, e.g., digital ECG data, collected from a patient in order to determine SCD risk.

The data preprocessor 122 may process input digital ECG-type data. Such preprocessing may include detrending, denoising, and normalization.

The ECG-derived model generator 124 may generate one or more mathematical models in the form of ECG-derived models, which include linear and nonlinear models, using linear and nonlinear modeling techniques, from the preprocessed digital ECG-type data.

The ECG-derived control model system generator 126 may incorporate system control operation features into the ECG-derived models, to generate, respectively, ECG-derived control model systems. The determinant 128 may determine stability/instability of the ECG-derived control system models, by analyzing responses of the ECG-derived control model systems to impulses.

The SCD risk determinator 130 may generate an SCD risk determination for any individual, which is an overall SCD risk value based on results of the stability/instability determinations for the ECG-derived control model systems constructed using of the individual's input digital ECG-type data.

A clinical trial can be designed to determine the overall sensitivity and specificity of the technology described herein. Such a clinical study may include 300 patients from which digital ECG-type data is collected, where the patients may be separated into three patient groups with 100 per group. The first group of digital ECG-type data may be obtained from 100 patients with no history of heart disease and no history of a sudden cardiac arrest (SCA)/sudden cardiac death (SCD)-type event. The second group of digital ECG-type data may be obtained from 100 patients with a history of heart disease, but no history of SCA/SCD. The third group of digital ECG-type data may be obtained from 100 patients with or without a history of heart disease, but with a history of a SCA or SCD-type event. With this data, the technology discussed herein is used to determine an SCD risk score based upon the relative stability/instability of all models designed corresponding to the input digital ECG-type data obtained from each subject of the study. The sensitivity and specificity of the technology described herein is determined by comparing the calculated SCD risk score of each subject to the subject group to which each belongs.

For instance, the apparatus 120 may be implemented in an individual apparatus, e.g., an ECG device, a general monitoring device, a Holter-type recording device, a PC chip, an ICD, or ATP-ICD (antitachycardia pacing ICD), SCD ablation equipment, etc., or as a self-contained unit.

Figure 2:
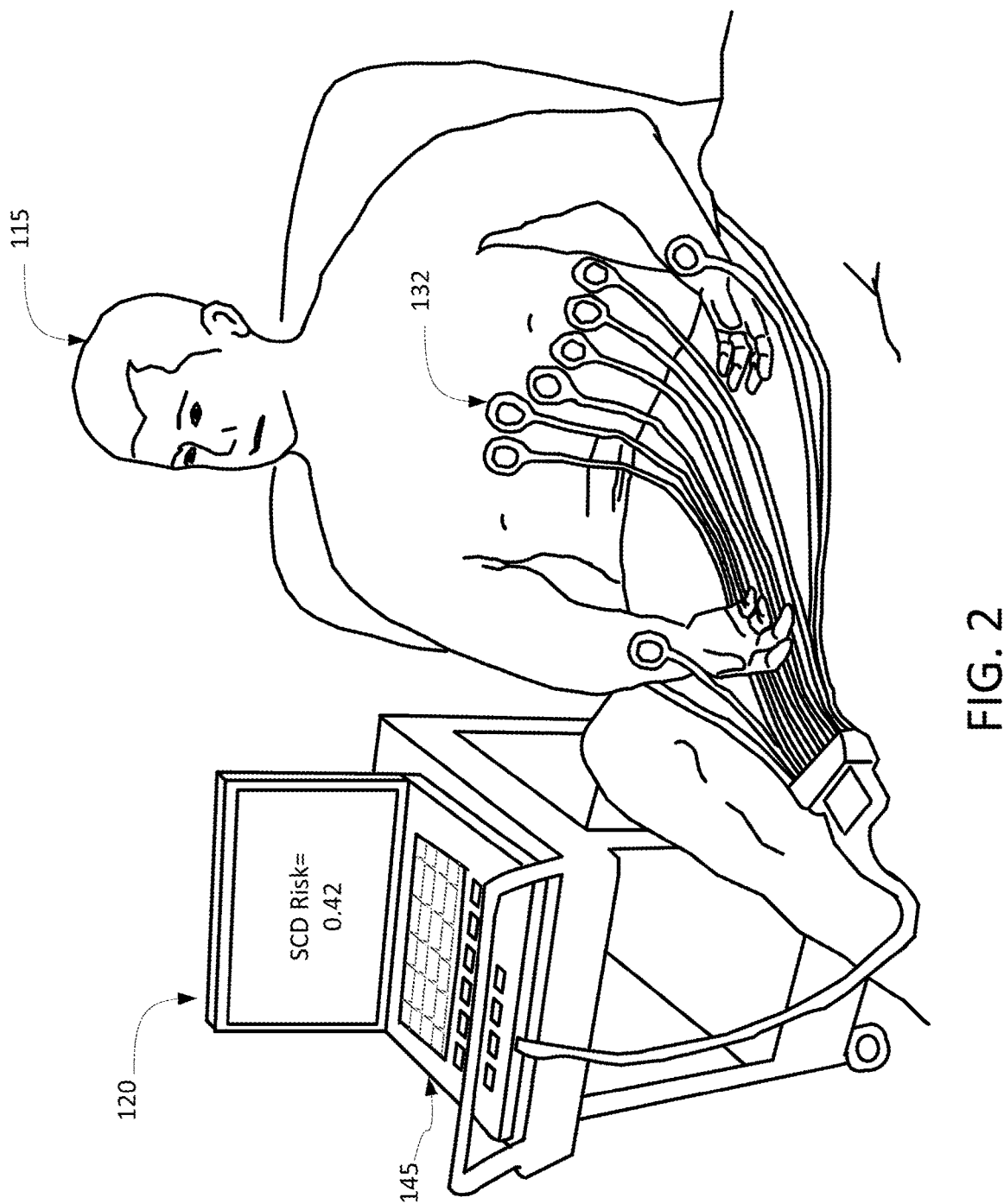
FIG. 2 shows an example clinical application of the apparatus of FIG. 1 in accordance with the present technology.

In some examples, the apparatus 120 may be used once or on multiple occasions in any given individual or many different individuals. Thus, the apparatus 120 can be a tool in clinical practice. For instance, as illustrated in FIG. 2, the apparatus 120 may operate in concert with a standard ECG device 145 that measures the digital ECG data of an individual 115 via electrodes 132. The apparatus 120 may determine the individual's risk for SCD and display on a screen this SCD risk value.

Figure 3:
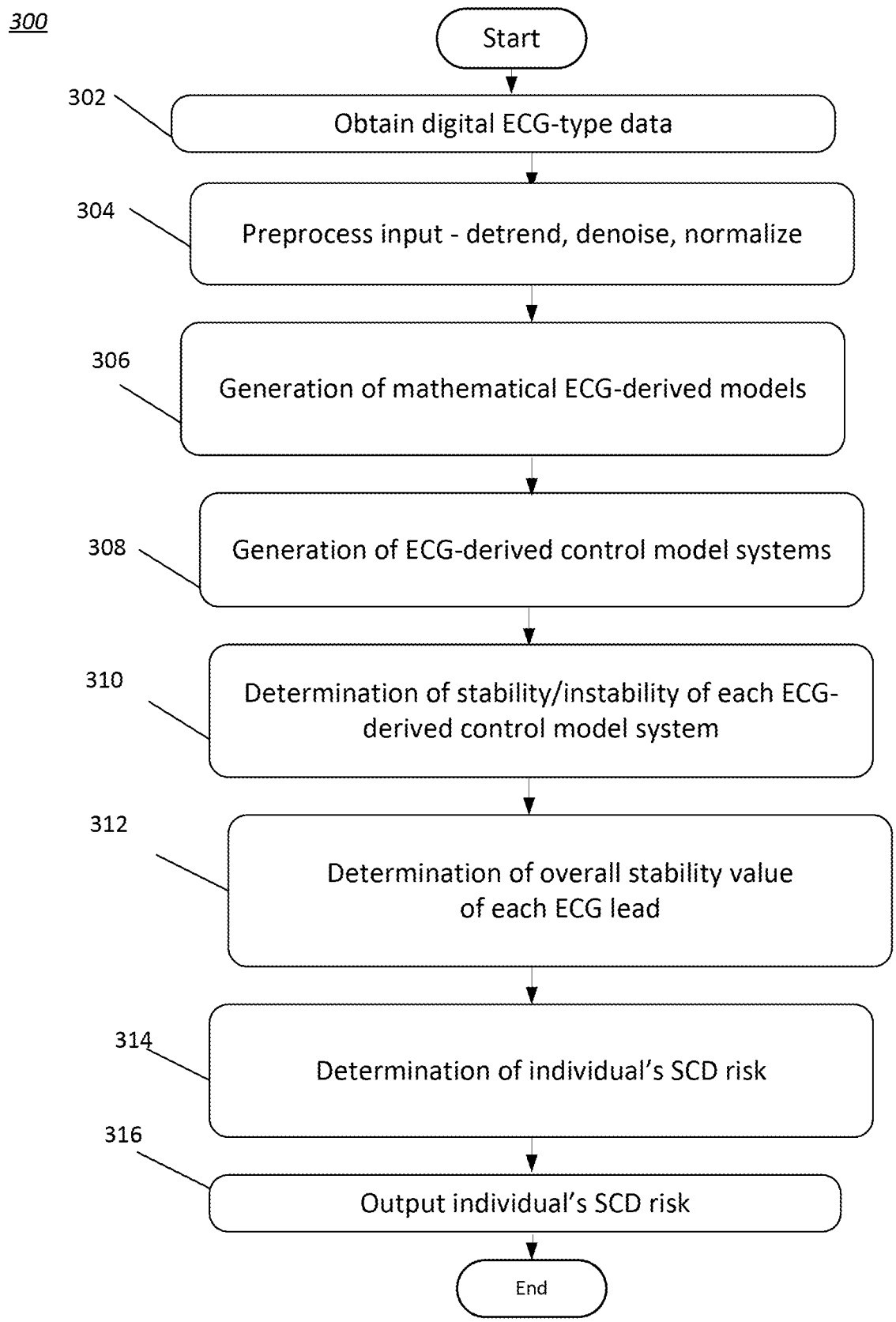
FIG. 3 illustrates a flow chart of an overall process performed by an SCD risk determination apparatus in accordance with the present technology.

FIG. 3 is a flowchart that illustrates an embodiment of a method of operation of the present technology. Methods illustrated in the flow chart of FIG. 3 and other flowcharts discussed herein may be executed by processors. In some examples, methods illustrated in each flow chart may be carried out periodically, continuously, as needed, as triggered, or in another manner. Each method may include one or more operations, functions, or actions as illustrated by one or more of the blocks. A block may represent a process of information, a transmission of information, or a combination thereof.

In a flowchart, although the blocks are illustrated in a sequential order, these blocks may also function in parallel or in a different order than those described herein, depending on the functionalities involved. Also, the various blocks may be combined into fewer blocks, divided into additional blocks, sub-blocks, or omitted based upon the desired implementation. Furthermore, blocks illustrated in various flow charts may be combined with one another, in part or in whole, based on the functionalities involved.

Referring to FIG. 3, at block 302, the data preprocessor 122 may obtain digital ECG-type data unique to a patient. The digital ECG-type data obtained for generating the digital ECG-derived models is not derived from any ECG tracings.

At block 304, as discussed in detail below, the preprocessor 122 may perform preprocessing on the digital ECG-type data in a manner optimal for use in SCD risk determination. Such preprocessing may include detrending, denoising, and normalization using techniques which may include FIR (Finite Impulse Response) as well as wavelet packet filtering.

At block 306, the generator 124 may generate multiple ECG-derived models for each preprocessed (by block 304) digital ECG-type data sample obtained for each ECG lead used to measure an ECG of the patient. The ECG-derived models then may be tested by the generator 104 for accuracy, validation and prediction.

At block 308, the generator 126 may, following verification and validation of the digital ECG-derived models, modify the digital ECG-derived models to include system control operations, to obtain digital ECG-derived control model systems corresponding to each digital ECG-derived model. For example, negative feedback loops and PIDs (proportional integral derivative) may be incorporated into each digital ECG-derived control model system, and PID tuning may be completed.

At block 310, the determinant 128 may determine system stability or instability of each digital ECG-derived control model system for each digital ECG data sample for each digital ECG lead of a patient, using a variety of stability/instability determination techniques. For example, the determinant 128 may mathematically apply electrical impulses in the form of perturbations to the digital ECG-derived control model systems, and analyze the results of the perturbations which are outputs of the digital ECG-derived control model systems, to determine system stability or instability of the digital ECG-derived control model systems. In one embodiment, the system stability analyses may use a variety of control theory techniques such as BIBO (bounded input—bounded output) methods, Nyquist and Bode plots, Routh-Hurwitz criteria, pole transform function analysis, eigenvalue analysis, robust margin stability, and Lyapunov stability methods.

At block 312, the determinator 130 may calculate an overall stability value for each digital ECG lead of the individual, based on the stability determined for the digital ECG-derived control model systems respectively corresponding to the digital ECG leads.

At block 314, the determinator 130 may determine a determined SCD risk for the individual, based on the overall stability values of the individual.

In one embodiment, an overall stability is determined based upon all control model systems developed for each digital ECG lead of each individual being studied. From these values, the risk for SCD for any given individual/digital ECG is determined.

In an embodiment in which the present technology is implemented in a study of 300 patients grouped into three groups as described above, SCD risk for each individual/digital ECG in the study is obtained. The sensitivity and specificity of these SCD risk values may be determined and verified, by revealing the patient group from which each patient in the study belongs.

At block 316, the determinator 130 may output the SCD risk for the individual, for example, for rendering on a display.

2. SCD Risk Determination Apparatus

2.1 General Operation of the SCD Risk Determination Apparatus

As described earlier, the processes of the SCD risk determination apparatus 120 may include generating linear and nonlinear mathematical models for any given individual/ECG based upon the input digital ECG-type data obtained from the individual. This may be performed in several steps.

Digital ECG data can be obtained either directly from one or more digital ECG leads, or from any skin sensor. At a first step, the device may use as input digital ECG data. This data may be obtained in one example from a standard, resting 12-lead digital ECG machine.

In one embodiment, the digital ECG lead placement is the standard ECG lead placement. In this embodiment, the apparatus can operate upon 12 digital ECG signals from an individual.

At a second step, the digital ECG data obtained from the patient, which may be stored in the memory of the apparatus, may be preprocessed by a preprocessor of the apparatus. The preprocessor may perform preprocessing in a manner to modify the input data into a format optimal for SCD risk determination. The preprocessing may include detrending, denoising, and normalization. This is accomplished using techniques including wavelet packet analysis. This extensive preprocessing may result in a data form optimal for control model system construction and ultimate SCD risk determination, according to the technology described herein.

Subsequently, all of the fully preprocessed digital ECG-type data may then be further operated upon in a manner which determines SCD risk in a given individual.

The generation of the ECG-derived models and ECG-derived control model systems may be performed in the apparatus such as in a processing unit thereof. In such a processing unit, the preprocessed digital ECG-type data is completely operated upon. A single or multiple distinct model(s) are constructed corresponding to the preprocessed digital ECG data corresponding to each ECG lead of each individual.

In some embodiments, the ECG-derived models may be generated using numerous techniques, including, but not limited to system identification methods. Linear models may include parametric models, impulse-response models, and frequency-response models, such as state-space, transfer functions, and spectral models. In addition, models may be generated based on AR (Auto Regression), ARMA (Auto Regression Moving Average), and polynomial-based systems. In addition, linear modeling techniques may include some or all of the following: state space, time domain and frequency domain methods. Further, nonlinear models may be constructed using techniques such as nonlinear auto regression exogenous (ARX), auto regressive integrated exogenous (ARIX), ARIMAX exogenous, transfer functions, Hammerstein-Wiener methodology and Box-Jenkins (BJ) techniques.

The processing, by using one of more the above methods and model generation techniques, may create mathematical models based upon an individual's digital ECG-type data. The digital ECG-derived models thus obtained are unique for every lead of every ECG of every individual.

In all cases, the digital ECG-derived models are verified and validated.

2.2 Example Components of Apparatus 120

Figure 4:
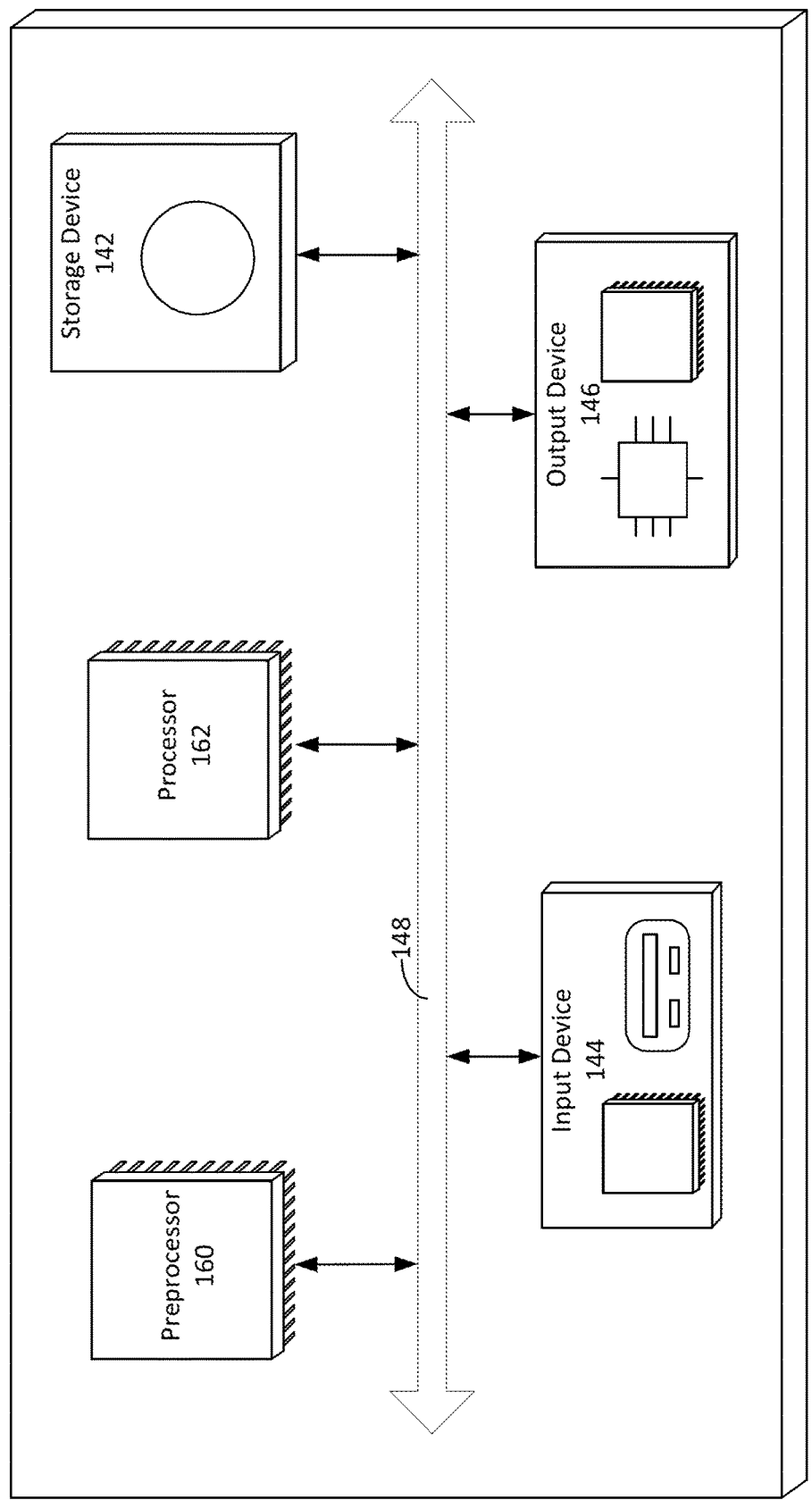
FIG. 4 shows a component diagram of an SCD risk determination apparatus in accordance with the present technology.

FIG. 4 is a schematic diagram of an exemplary implementation of the apparatus 120. The apparatus 120 may include one or more of the following components: one or more preprocessors such as preprocessor 160, one or more processors 162, a storage device 142, an input device 144, and an output device 146. Components of the apparatus 120 may be communicatively coupled together in either a wired or wireless fashion. In some cases, the methodologies of the processing components may be achieved in a single processor or multiple processors. In one example as illustrated in FIG. 4, the components may be coupled together by a system bus 148. A detailed description of each component is as follows.

2.2.1 Preprocessor and Processor

The preprocessor 160 and processor 162 may control and execute the functions of the blocks of FIG. 3. For instance, the preprocessor 160 may perform the following functions, including detrending, denoising, and normalization of the digital input data. The processor 162 may perform the following operations, including generating a mathematical model based upon preprocessed (by block 304) digital ECG-type data as a digital ECG-derived model using linear and nonlinear modeling methods and techniques, generating digital ECG-derived control model systems by respectively modifying the digital ECG-derived models for system control operation, determining stability of the digital ECG-derived control model systems by methods including analyzing responses thereto to perturbation, and determining SCD risk for the individual/ECG based on the stability determinations. The preprocessor 160 and processor 162 may be of any type including but not limited to a general purpose preprocessor or processor and a special purpose or dedicated preprocessor or processor, e.g., an application-specific integrated circuit (ASIC), a digital signal processor (DSP), a graphical processing unit (GPU), a floating point processing unit (FPU), and the like. The preprocessor 160 and the processor 162 may refer to a single processor, or a collection of processors of the same type or various types, which may or may not operate in a parallel-processing mode.

The preprocessor 160 and the processor 162 may communicate with other components of the apparatus 120. In one example, the preprocessor 160 and the processor 162 may execute computer-readable instructions or other instructions stored in the storage device 142. The preprocessor 160 and the processor 162 may read and write the data during execution of the computer-readable instructions. In another example, the preprocessor 160 may act upon input signals provided by the input device 144.

2.2.2 Storage Device of Apparatus

The storage device 142 may provide storage data for the apparatus 120 by using one or more non-transitory computer-readable media. The computer-readable media may store volatile data, non-volatile data, or a combination thereof. Some computer-readable media may store data for a short period of time. Other computer-readable media may store data persistently for a long period of time.

The computer-readable media may include primary storage, secondary storage, or a combination thereof. The primary storage may be simply referred to as memory, which is directly accessed by the preprocessor 160 and the processor 162. The secondary storage may be indirectly accessed by the preprocessor 160 and processor 162 via the primary storage.

The computer-readable media may be of different types including random-access memory (e.g., SRAM and DRAM), read-only memory (e.g., Mask ROM, PROM, EPROM, and EEPROM), non-volatile random-access memory (e.g. flash memory), a magnetic storage medium, an optical disc, a memory card, a Zip drive, a register memory, a processor cache, a solid state drive (SSD), and a redundant array of independent disks (RAID), among other possibilities.

The storage device 142 may store one or more computer-readable instructions, data, applications, processes, threads of applications, program modules and/or software, which are accessible or executable by the preprocessor 160 and the processor 162 to perform at least part of the herein-described methods and techniques.

By way of example, the computer-readable instructions in the storage device 142 may include logic that generates digital ECG-derived models and digital ECG-derived control model systems, in one example applies impulses to digital ECG-derived control model systems, and analyzes responses to the impulses for determining SCD risk information.

Examples of data stored in the storage device 142 may include but are not limited to variables, results and data obtained from one or more digital ECG devices, the digital ECG-derived models and digital ECG-derived control model systems, and equations, formula and algorithms used to determine model control system stability/instability.

2.2.3 Input Device

The input device 144 may refer to one or more peripheral devices configured to receive information from individuals. The input device 144 may communicate such information to other components of the apparatus 120.

By way of example, the input device 144 may be one or more digital ECG leads, a digital ECG device, such as a standard resting 12-lead digital ECG device or device with more or fewer of such electrode leads. The input device 144 may also include user input components such as a keyboard, keypad, touch pad, point device, track ball, joystick, voice recognition device, touch-sensitive surface, microphone, digital camera, mouse, buttons, switch, scroll-wheel, scanner, GPS receiver, movement sensor, location sensor, infrared sensor, optical sensor, Radio Frequency identification (RFID) system, and wireless sensor, among others. In some examples, the input device 144 may include an external defibrillator or implantable cardioverter-defibrillator (ICD or ATP-ICD).

The input device 144 may provide a number of different types of digital input data, such as a digital ECG measurement, an electrogram (EGM) measurement, audio data from a microphone, text data from a keypad, video or image data from a camera, and gesture data from a touchpad, just to name a few. This data may be gathered from clinical studies on groups of individuals such as with other devices and transferred in digital form to the preprocessor 160 via the input.

2.2.4 Output Device

The output device 146 may communicate one or more outputs of the determinator 130. The output device 146 may include output components such as a digital output file, a digital output storage device, a visual display, audio transducer, light indicator, tactile transducer, printer, light bulb, and vibration generator, among others. The output device 146 may provide a number of different types of output data, such as digital data, visual output via a display, audio output via a speaker, and tactile output via a vibration generator, among others.

Also, the output device may be a digital storage device. In some examples, the output device 146 may include one or more audio transducers in the following forms: a speaker, headset, jack, earphone, and audio output port.

2.3 Example Logic and Methods

The apparatus 120 may include computer algorithms such as computer-readable instructions, ASICs, FPGAs, DSPs, integrated circuits, modules, firmware, or a combination thereof, among other possibilities, to implement the functions of the present technology, for example, as illustrated in flow diagram 300 and executed by the preprocessor 160 and preprocessor 162 of the apparatus 120. These computer algorithms may be implemented in a signal bearing non-transitory computer-readable storage medium in a variety of forms. The apparatus 120 may perform only once or be reused several times to obtain digital ECG-type data from patients, such as of different clinical studies, and determine SCD risk values by processing such ECG-type data.

The preprocessor 160 may perform ECG data noise removal, detrending, baseline drift elimination and denoising.

2.3.1 Preprocessor 160

Figure 5:
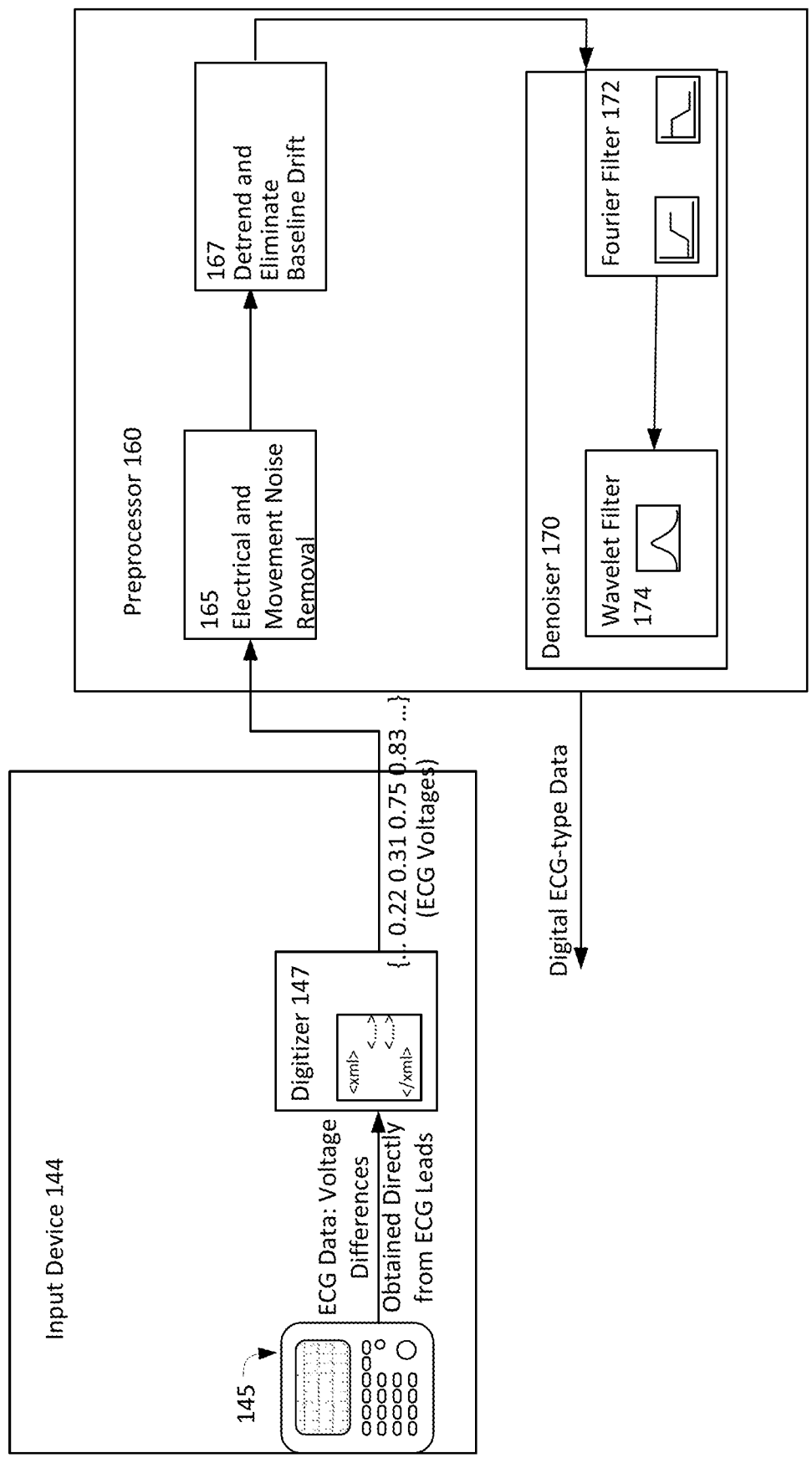
FIG. 5 is a block diagram of an example implementation of selected components of the apparatus of FIG. 4.

Referring to FIG. 5, a schematic illustration of an exemplary configuration of the preprocessor 160 of the apparatus 120 is shown. As discussed above, the preprocessor 160 may perform processing for digital ECG-type data detrending, normalization, baseline drift elimination and denoising. The preprocessor 160 may preprocess digital ECG measurements, such as may be obtained from a clinical study or individual patient measurement. The digital ECG measurements may include all of the digital information obtained from all leads of any digital ECG's device or from the digital ECG lead itself. As illustrated in FIG. 5, the digital ECG measurements of any human subject may be obtained from an ECG device 145 and digitizer 147 which are part of the input device 144 of the apparatus 120. The digital ECG device 145 may be a standard resting 12-lead digital ECG device or such a measurement device of any other number of leads. Alternatively, the digital ECG device 145 may be a management system, such as the MUSE Cardiology Information System by GE Healthcare, which stores and manages digital ECG measurements output by one or more digital ECG devices. The digital ECG measurement obtained from an individual may include measured voltages obtained from each lead. For instance, the digital ECG measurement extracted from a standard resting 12-lead digital ECG device for one individual may have twelve sequences representing digital 12-lead ECG measurements obtained from the individual. A sequence may represent the voltage measures as a function of time associated with one of the twelve leads: Lead I, Lead II, Lead III, Lead aVR, Lead aVL, Lead aVF, Lead V1, Lead V2, Lead V3, Lead V4, Lead V5, and Lead V6. For example, each individual in three groups of patients in a study, as described above, may have twelve sequences. Each digital ECG measurement may include measurements taken from a period of time (e.g., approximately 10 seconds, or other suitable time periods). In an alternative embodiment, the unpreprocessed digital data may be obtained from a standard data acquisition (DAQ) device.

As illustrated in FIG. 5, the preprocessor 160 may include one or more of the following subunits: a noise removal subunit 165, a detrending and baseline drift eliminator (DTBDE) subunit 167 and a denoiser subunit 170.

The noise removal subunit 165 may receive digital ECG measurements, and remove electrical noise and movement artifact noise using modification of the techniques of ECG data normalization as well as wavelet packet techniques. The DTBDE subunit 167 may receive digital data output from the subunit 165, following processing by the subunit 165, and further process the received data for eliminating baseline drift and denoising.

The denoising subunit 170 may receive digital data output from the subunit 167, following processing by the subunit 167, and remove signal noise using a Finite Impulse Response (FIR) digital filter. The signal noise may include mechanical noise, respiration-related noise and white noise. In one embodiment, the data received by the denoiser subunit 170 may be filtered by a Fourier filter 172 and then wavelet packet filtering may then performed by the preprocessor 160 for further signal denoising. The wavelet filters 174 may use several wavelet families at a variety of decomposition levels to further denoise the signals. The wavelet filter 174 may employ entropy methods to obtain optimal thresholding in order to obtain ideal denoising. The wavelet filter 174 may include implementation of a discrete wave transform. Alternatively, the wavelet filter 174 may include implementation of a continuous wavelet transform. Parameters associated with the continuous wavelet transform may be adjusted either automatically or manually.

2.3.2 Processor

Referring again to FIG. 4, the processor 162 may receive as input the preprocessed ECG-type data output of the preprocessor 160. In the processor 162, linear and nonlinear mathematical models of the preprocessed ECG-type data may be generated. In addition, the processor 162 may implement functions of the generator 126, the determinant 128 and the determinator 130 to perform mathematical operations with regard to and using the digital ECG-derived models to determine SCD risk for the patient.

The processor 162 may function to quantitatively determine the risk in any given individual of the occurrence of SCD, using the digital ECG-derived control model systems of the individual. For example, once the digital ECG-derived model systems for the patient are generated, the processor 162 may determine a SCD risk of the individual to which the digital ECG-derived control model systems correspond.

In one embodiment, the processor 162 may function by testing the digital ECG-derived models for accuracy, validation, and prediction. The sensitivity and specificity of the SCD risk for an individual/digital ECG may be determined by multiple quantitative analyses of the results generated by applying a variety of methods for determining the stability/instability of the corresponding digital ECG-derived control model systems. The perturbations may include step, transfer and impulse response methods.

From such analyses, overall stability/instability values for each of the ECG leads for an individual/ECG, based on the stability of the digital ECG-derived control model systems determined for the respective ECG leads is determined.

The individual's risk for SCD may be quantitatively derived from the overall stability/instability values for each of the digital ECG-derived control model systems corresponding to the individual determined from the results of these analyses. In other words, digital ECG-derived control model system stability/instability is determined and stability/instability values obtained from this determination are quantitatively transformed into SCD risk values.

In this manner, the sensitivity and specificity of an SCD risk apparatus according to the present technology may be determined to be greater than 95%.

Based upon the analysis of the results obtained by implementing the present technology, the relative risk of the patient in a study for experiencing SCD may be quantitatively determined.

In one embodiment, the risk values corresponding to each ECG-type data sample may be plotted as a scatter plot against the patient group from which the sample was obtained. From the scatter plot, the sensitivity and specificity as well as corresponding p-value may be calculated for the present technology of determining SCD risk.

Advantageously, according to the technology of the disclosure, risk of any individual for SCD may be quantitatively determined with sensitivity/specificity >95% with p-value <0.001.

In some cases, the output of the apparatus 120 may be a number ranging from zero to one. In such an example, SCD risk scores correlate with SCD risk as follows:

| SCD RISK SCORE | SCD RISK |
| --- | --- |
| 0.00-0.10 | very low risk |
| 0.11-0.40 | low risk |
| 0.41-0.70 | moderate risk |
| 0.71-1.00 | high risk |

Although the output may be a real number, in some versions an index may be implemented on a suitable scale for a similar stratification of the risk. Similarly, the output may include a message such as text identifying the nature of the risk (e.g., very low, low, moderate, high etc.). Other formats for stratification may optionally be implemented.

3. Other Implementations

The implementations of each of the components in the apparatus 120, such as shown in FIG. 1, including the processes, parts, units and subunits thereof described of are merely illustrative, and not meant to be limiting. Each apparatus may include other parts, units, subunits, or variations thereof. For instance, each of the data preprocessor 122, the generators 124 and 126, the determinant 128 and the determinator 130 may be divided into additional parts, units, or subunits.

According to some aspects of the technology, the apparatus 120, alone or in combination with other subunits, may be a plug-in application to a standard digital ECG device, such as a standard resting 12-lead digital ECG. Moreover, the processes and methods described herein may be performed in whole or in part by a computer or other processing apparatus that may include integrated chips, a memory and/or other control instruction, data or information storage medium. For example, programmed instructions encompassing such methodologies may be coded on integrated chips in the memory of the device. Such instructions may also or alternatively be loaded as software or firmware using an appropriate data storage medium. With such an apparatus, the device can determine digital ECG-derived models from previously measured and received digital ECG data, such as data measured by a discrete measuring device.

In some cases, the apparatus may be part of an ATP-ICD (anti-tachycardia pacing (ATP) ICD). In some cases, an apparatus in accordance with aspects of the present technology may be coupled to a defibrillator, e.g., by wireless communication, so as to receive EGM-type data for testing purposes. Thus, while a 12-lead digital ECG has previously been described, the apparatus according to aspects of the present technology may be configured to operate on 3-lead EGM signals or any other number of leads or electrode measurements.

In one embodiment, the present technology may be implemented completely independent of any digital ECG machine, and obtain input from any single, three or twelve digital ECG-type skin leads.

Figure 6:
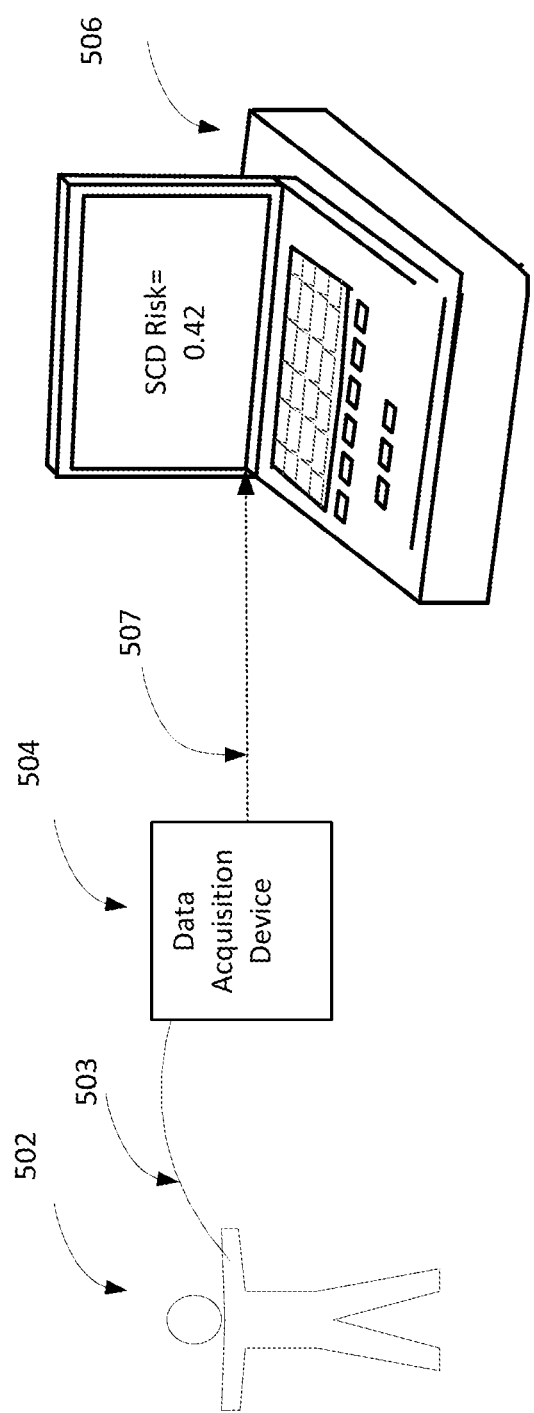
FIG. 6 is an exemplary implementation of a SCD risk determination apparatus in accordance with the present technology.

In one embodiment, referring to FIG. 6, aspects of the present technology may be implemented in an apparatus 506, which has the same or similar functionalities as the apparatus 120 described above. The apparatus 506 may be communicatively coupled to a data acquisition device 504 (DAQ) external to and independent of the apparatus 506. The DAQ 504 may be utilized to obtain ECG-type data from an individual 502 using one or more ECG leads 503, and provide the ECG-type data, without any preprocessing so as to be in unpreprocessed form as unpreprocessed ECG-type data as described above, to the apparatus 506, via a wireless or wired transmission medium 507. The apparatus 506, based on the unpreprocessed ECG-type data, may determine SCD risk according to the present technology.

In another embodiment, referring to FIG. 7, aspects of the present technology may be implemented in an apparatus 600, which is in the form of a smartwatch having communication capabilities and includes the same or similar functionalities of determining SCD risk as the apparatus 120 described above. The functions of the present technology to determine and output determined SCD risk may be included in an application (APP) stored in a memory of the apparatus 600 and executed by a processor of the apparatus 600. In such embodiment, the apparatus 600 may include one or more skin-potential sensors (not shown) for obtaining ECG-type data from the individual when the individual is wearing the smartwatch apparatus, and then determine a determined SCD risk according to the present technology from such data.

In one embodiment, the digital ECG-derived models and control model systems may be generated by an apparatus using digital EGM data rather than digital ECG data as input. Such an apparatus for determining a SCD risk value from the digital ECG-derived control model systems could be incorporated into an ATP-ICD device to enable anti-tachycardia pacing (ATP) prior to the onset of SCD (SCA), thereby preventing any occurrence of ventricular tachycardia are ventricular fibrillation.

In addition, the technology of the disclosure may function in real time, and therefore be used to guide ventricular ablation procedures. The technology of the disclosure may be used to determine at the time of an ablation procedure (ventricular ablation performed to lower the incidence of SCD in patients at risk for SCD) whether the patient risk for SCD has been successfully reduced and the procedure can be ended. At present, electrical inducibility of ventricular tachycardia is the method used to predict the success of ventricular ablation. This technique has not been demonstrated to be a good for determining SCD.

4. Some Potential Advantages of the Present Technology

The present technology for generating mathematical models and control model systems from digital ECG-type data and quantitatively determining an individual's risk for SCD based on an analysis of the stability/instability of these digital ECG-derived control model systems has many advantages.

First, the present technology may provide noninvasive risk stratification in individuals with high sensitivity and high specificity.

Second, the device may identify critical information hidden within complex data outputs/collections. It may identify digital electrocardiogram data responsible or otherwise associated with the onset of Sudden Cardiac Death (such as those measured within a resting, multi-lead digital ECG).

Third, the present technology may perform risk-stratification in individuals of all risk levels, including no risk, low risk, intermediate risk and high risk. In particular, the present technology may identify individuals at risk for SCD that are not detectable by prior known techniques.

Fourth, the present technology may identify individuals at risk for SCD with high specificity and sensitivity levels not previously achieved.

Fifth, the present technology may do so without use of known factors—alone or in combination—presently used in SCD risk-stratification, including left ventricular ejection fraction (LVEF), signal-averaged electrocardiogram (SAECG), microvolt T-wave alternans (MTWA), ambulatory ECG monitoring, heart failure, metabolic factors and autonomic control. As such, the present technology obviates the shortcomings of these technologies as discussed in the background section, although in some embodiments the assessment may be combined with known methods.

Sixth, by identifying individuals at risk for SCD, the present technology has a transformational impact in the initiation of appropriate treatment of SCD (e.g., ICD implantation) and thereby may greatly reduce the incidence of SCD.

Seventh, the present technology poses no risk to any individual, other than the insignificant risk of undergoing a standard ECG.

Eighth, the present technology may successfully calculate SCD risk in all individuals, regardless of whether the individuals have experienced cardiac surgery, and regardless of their clinical history, including history of myocardial infarction, atherosclerotic heart disease, cardiomyopathy, cardiac rhythm, and cardiac condition abnormalities. For example, unlike most of the presently available risk-stratification technologies, the technology described herein can be performed and used to determine SCD risk in individuals with common cardiac rhythm disorders, including atrial fibrillation, premature ventricular contractions (PVCs), as well as bundle branch blocks and complete heart block.

Ninth, the present technology may be used in individuals with no known risk factors for SCD. This includes athletes at the middle school, high school, college and professional level, relatives of individuals who have experienced SCD as well as part of any individuals undergoing a routine physical exam.

Tenth, the present technology may be used to follow the progression of SCD risk in any individual.

Finally, the general principles used in the technology described herein may be used to extract important parameters and information from a vast variety of signals, including speech, sound, graphic, visual, mechanical, and electrical devices.

5. Conclusion

The present technology may also be configured as below.
(1) A method for quantitative determination of Sudden Cardiac Death (SCD) risk using digital electrocardiogram (ECG)-type data of an individual, the method including steps of:

(a) preprocessing digital ECG-type data by detrending, denoising, and normalizing, to obtain preprocessed ECG-type data; (b) generating a plurality of mathematical digital ECG-derived models corresponding to the preprocessed digital ECG-type data; (c) generating digital ECG-derived control model systems corresponding to each digital ECG-derived model; (d) determining system stabilities of the digital ECG-derived control model systems by a plurality of techniques; and (e) determining, based on the system stabilities, a derived SCD risk for the individual.

(2) The method according to (1), further including: determining the SCD risk for the individual with sensitivity and specificity >95% and p-value <0.001.

(3) The method according to (1) or (2), wherein the preprocessing of the digital ECG-type data includes: removing movement and electrical noise from the digital ECG-type data, to obtain first preprocessed data; detrending and eliminating baseline drift from the first preprocessed data, to obtain second preprocessed data; and denoising the second preprocessed data.

(4) The method according to any one of (1) to (3), wherein the denoising is by at least one of a Finite Impulse Response (FIR) filter or a wavelet denoising method employing an entropy calculation to optimize a threshold setting.

(5) The method according to any one of (1) to (4), wherein the denoising is of at least one of mechanical noise, respiration artifacts or white noise.

(6) The method according to any one of (1) to (5), wherein the digital ECG-type data for the individual is obtained using a standard resting digital 12-lead ECG, or a single lead or three lead skin sensor input independent of any digital ECG device in concert with or without an external data acquisition (DAQ) device.

(7) The method according to any one of (1) to (6), wherein the digital ECG-derived models are generated using linear and nonlinear modeling methods, and
wherein the digital ECG-derived models are modified for system control operation to obtain the digital ECG-derived control model systems.

(8) The method according to any one of (1) to (7), wherein the determining of the system stabilities includes analyzing responses of the digital ECG-derived control model systems to impulses.

(9) The method according to any one of (1) to (8), wherein the digital ECG-derived control model systems include negative feedback loops.

(10) An apparatus for quantitative determination of sudden cardiac death (SCD) risk using digital electrocardiogram (ECG)-type data of an individual, the apparatus including: circuitry configured to control: preprocessing digital ECG-type data by detrending, denoising and normalizing, to obtain preprocessed ECG-type data; generating a plurality of mathematical digital ECG-derived models corresponding to the preprocessed digital ECG-type data; generating digital ECG-derived control model systems corresponding to each digital ECG-derived model; determining system stabilities of the digital ECG-derived control model systems, by a plurality of techniques; and determining, based on the system stabilities, a derived SCD risk for the individual.

(11) The apparatus according to (10), wherein the circuitry is configured to control determining the SCD risk for the individual with sensitivity and specificity >95% and p-value <0.001.

(12) The apparatus according to (10) or (11), wherein the preprocessing of the digital ECG-type data includes: removing movement and electrical noise from the digital ECG-type data, to obtain first preprocessed data; detrending and eliminating baseline drift from the first preprocessed data, to obtain second preprocessed data; and denoising the second preprocessed data.

(13) The apparatus according to any one of (10) to (12), wherein the denoising is by at least one of a Finite Impulse Response (FIR) filter or a wavelet denoising method employing an entropy calculation to optimize a threshold setting.

(14) The apparatus according to any one of (10) to (13), wherein the denoising is of at least one of mechanical noise, respiration artifacts or white noise.

(15) The apparatus according to any one of (10) to (14), wherein the digital ECG-type data for the individual is obtained using a standard resting digital 12-lead ECG, or a single lead or three lead skin sensor input independent of any digital ECG device in concert with or without an external data acquisition (DAQ) device.

(16) The apparatus according to any one of (10) to (15), wherein the digital ECG-derived models are generated using linear and nonlinear modeling methods, and
wherein the digital ECG-derived models are modified for system control operation to obtain the digital ECG-derived control model systems.

(17) The apparatus according to any one of (10) to (16), wherein the determining of the system stabilities includes analyzing responses of the digital ECG-derived control model systems to impulses.

(18) The apparatus according to any one of (10) to (17), wherein the digital ECG-derived control model systems include negative feedback loops.

(19) A non-transitory storage medium on which is recorded a program executable by a computer, the program including: preprocessing digital ECG-type data by detrending, denoising, and normalizing, to obtain preprocessed digital ECG-type data; generating a plurality of mathematical digital ECG-derived models corresponding to the preprocessed digital ECG-type data; generating digital ECG-derived control model systems corresponding to each digital ECG-derived model; determining system stabilities of the digital ECG-derived control model systems by a plurality of techniques; and determining, based on the system stabilities, a derived SCD risk for the individual.

(20) The medium according to (19), wherein the program further includes: generating the digital ECG-derived models using linear and nonlinear modeling methods, and modifying the digital ECG-derived models for system control operation to obtain the digital ECG-derived control model systems.

Although aspects of the disclosure herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:
1. A method for quantitative determination of sudden cardiac death (SCD) risk using digital electrocardiogram (ECG)-type data of an individual, the method comprising:
(a) preprocessing digital ECG-type data by detrending, denoising, and normalizing, to obtain preprocessed ECG-type data;

(b) generating a plurality of mathematical digital ECG-derived models corresponding to the preprocessed ECG-type data;

(c) generating digital ECG-derived control model systems corresponding to each mathematical digital ECG-derived model;

(d) determining stability of the digital ECG-derived control model systems by applying simulated impulses in a form of perturbations to the digital ECG-derived control model systems, and analyzing results of the perturbations' output by the digital ECG-derived control model systems;

(e) calculating overall stability values based on the determined system stabilities;

(f) determining, based on the overall stability values, a derived SCD risk for the individual; and (g) outputting the derived SCD risk on a display.

2. The method of claim 1, further comprising:
determining the SCD risk for the individual with sensitivity and specificity>95% and p-value <0.001.

3. The method of claim 1, wherein the preprocessing of the digital ECG-type data includes:
removing movement and electrical noise from the digital ECG-type data, to obtain first preprocessed data;
detrending and eliminating baseline drift from the first preprocessed data, to obtain second preprocessed data; and
denoising the second preprocessed data using wavelet transform.

4. The method of claim 3, wherein the denoising is by at least one of a finite impulse response (FIR) filter or a wavelet denoising method employing an entropy calculation to optimize a threshold setting.

5. The method of claim 4, wherein the denoising is of at least one of mechanical noise, respiration artifacts or white noise.

6. The method of claim 1, wherein the ECG-type data for the individual is obtained using a standard resting digital 12-lead ECG, or a single lead or three lead skin sensor input independent of any ECG device in concert with or without an external data acquisition (DAQ) device.

7. The method of claim 1, wherein the mathematical digital ECG-derived models are generated using linear and nonlinear modeling methods, and wherein the mathematical digital ECG-derived models are modified for system control operation to obtain the digital ECG-derived control model systems.

8. The method of claim 1, wherein the results are analyzed by using at least one of bounded input bounded output (BIBO) methods, Nyquist and Bode plots, Routh-Hurwitz criteria, pole transform function analysis, eigenvalue analysis, robust margin stability, or Lyapunov stability methods.

9. The method of claim 1, wherein the digital ECG-derived control model systems include negative feedback loops.

10. An apparatus for quantitative determination of sudden cardiac death (SCD) risk using digital electrocardiogram (ECG)-type data of an individual, the apparatus comprising:
circuitry configured to control:
preprocessing digital ECG-type data by detrending, denoising and normalizing, to obtain preprocessed ECG-type data;
generating a plurality of mathematical digital ECG-derived models corresponding to the preprocessed ECG-type data;
generating digital ECG-derived control model systems corresponding to each mathematical digital ECG-derived model;
determining system stabilities of the digital ECG-derived control model systems by applying simulated impulses in a form of perturbations to the digital ECG-derived control model systems, and analyzing results of the perturbations output by the digital ECG-derived control model systems; calculating overall stability values based on the determined system stabilities; and determining, based on the overall stability values, a derived SCD risk for the individual; and
generating an output displaying the derived SCD risk.

11. The apparatus of claim 10, wherein the circuitry is configured to control determining the SCD risk for the individual with sensitivity and specificity>95% and p-value <0.001.

12. The apparatus of claim 10, wherein the preprocessing of the digital ECG-type data includes:
removing movement and electrical noise from the digital ECG-type data, to obtain first preprocessed data;
detrending and eliminating baseline drift from the first preprocessed data, to obtain second preprocessed data; and
denoising the second preprocessed data.

13. The apparatus of claim 12, wherein the denoising is by at least one of a Finite Impulse Response (FIR) filter or a wavelet transform.

14. The apparatus of claim 13, wherein the denoising is of at least one of mechanical noise, respiration artifacts or white noise.

15. The apparatus of claim 10, wherein the digital ECG-type data for the individual is obtained using a standard resting digital 12-lead ECG, or a single lead or three lead skin sensor input independent of any digital ECG device in concert with or without an external data acquisition (DAQ) device.

16. The apparatus of claim 10, wherein the mathematical digital ECG-derived models are generated using linear and nonlinear modeling methods, and wherein the mathematical digital ECG-derived models are modified for system control operation to obtain the digital ECG-derived control model systems.

17. The apparatus of claim 10, wherein the results are analyzed by using at least one of bounded input bounded output (BIBO) methods, Nyquist and Bode plots, Routh-Hurwitz criteria, pole transform function analysis, eigenvalue analysis, robust margin stability, or Lyapunov stability methods.

18. The apparatus of claim 10, wherein the digital ECG-derived control model systems include negative feedback loops.

19. A non-transitory storage medium on which instructions are stored, the instructions when executed by one or more processors, cause the one or more processors to perform a method comprising:
preprocessing digital electrocardiogram (ECG)-type data by detrending, denoising, and normalizing, to obtain preprocessed ECG-type data;
generating a plurality of mathematical digital ECG-derived models corresponding to the preprocessed ECG-type data;
generating digital ECG-derived control model systems corresponding to each mathematical digital ECG-derived model;
determining system stabilities of the digital ECG-derived control model systems by applying simulated impulses in a form of perturbations to the digital ECG-derived control model systems, and analyzing results of the perturbations output by the digital ECG-derived control model systems;

calculating overall stability values based on the determined system stabilities;

determining, based on the overall stability values, a derived sudden cardiac death (SCD) risk for the individual; and generating an output to display the derived SCD risk.

20. The medium of claim 19, wherein the method further comprises:

generating the mathematical digital ECG-derived models using linear and nonlinear modeling methods; and modifying the mathematical digital ECG-derived models for system control operation to obtain the digital ECG-derived control model systems.

* * * * *